US011896361B2

(12) United States Patent
Kutsuna et al.

(10) Patent No.: US 11,896,361 B2
(45) Date of Patent: Feb. 13, 2024

(54) IMAGE GENERATING APPARATUS, IMAGE GENERATION METHOD, AND NONTRANSITORY COMPUTER-READABLE STORAGE MEDIUM STORING THEREIN IMAGE GENERATION PROGRAM

(71) Applicant: CANON MEDICAL SYSTEMS CORPORATION, Otawara (JP)

(72) Inventors: Hideaki Kutsuna, Kawasaki (JP); Hidenori Takeshima, Kawasaki (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 15 days.

(21) Appl. No.: 17/496,199

(22) Filed: Oct. 7, 2021

(65) Prior Publication Data
US 2022/0183582 A1    Jun. 16, 2022

(30) Foreign Application Priority Data
Dec. 10, 2020   (JP) .................... 2020-204769

(51) Int. Cl.
*A61B 5/055* (2006.01)
*G01R 33/561* (2006.01)

(52) U.S. Cl.
CPC .......... *A61B 5/055* (2013.01); *G01R 33/5611* (2013.01)

(58) Field of Classification Search
CPC ........... A61B 5/055; G01R 33/5611; G01R 33/56545; G01R 33/4824; G01R 33/4818; G01R 33/543; G01R 33/3621; G01R 33/483; G01R 33/5608; G01R 33/4826; G01R 33/565
See application file for complete search history.

(56) References Cited

U.S. PATENT DOCUMENTS

| | | | | |
|---|---|---|---|---|
| 2003/0052676 A1* | 3/2003 | Takahashi | .......... | G01R 33/5611 324/309 |
| 2006/0049829 A1* | 3/2006 | Takizawa | .......... | G01R 33/5611 324/309 |
| 2007/0182411 A1* | 8/2007 | Bammer | .......... | G01R 33/56308 324/307 |
| 2010/0039110 A1* | 2/2010 | Takahashi | .......... | G01R 33/5611 382/280 |
| 2015/0276906 A1* | 10/2015 | Wiesinger | .......... | G01R 33/4816 324/309 |

FOREIGN PATENT DOCUMENTS

JP    2020-115967 A    8/2020

* cited by examiner

*Primary Examiner* — Colin T. Sakamoto
*Assistant Examiner* — Tommy T Ly
(74) *Attorney, Agent, or Firm* — Oblon, McClelland, Maier & Neustadt, L.L.P.

(57) ABSTRACT

An image generating apparatus according to the embodiment includes processing circuitry. The processing circuitry acquires MR data acquired in read-out directions including a first read-out direction and a second read-out direction intersecting the first read-out direction, filter sensitivity distributions corresponding to the read-out directions and indicating distributions of sensitivity of a low-pass filter, and coil sensitivity distributions corresponding to coil elements used to acquire the MR data. The processing circuitry generates synthesis sensitivity distributions for the respective read-out directions by synthesizing the filter sensitivity distributions and the coil sensitivity distributions for the respective read-out directions. The processing circuitry generates an MR image based on the synthesis sensitivity distributions and MR data.

7 Claims, 8 Drawing Sheets

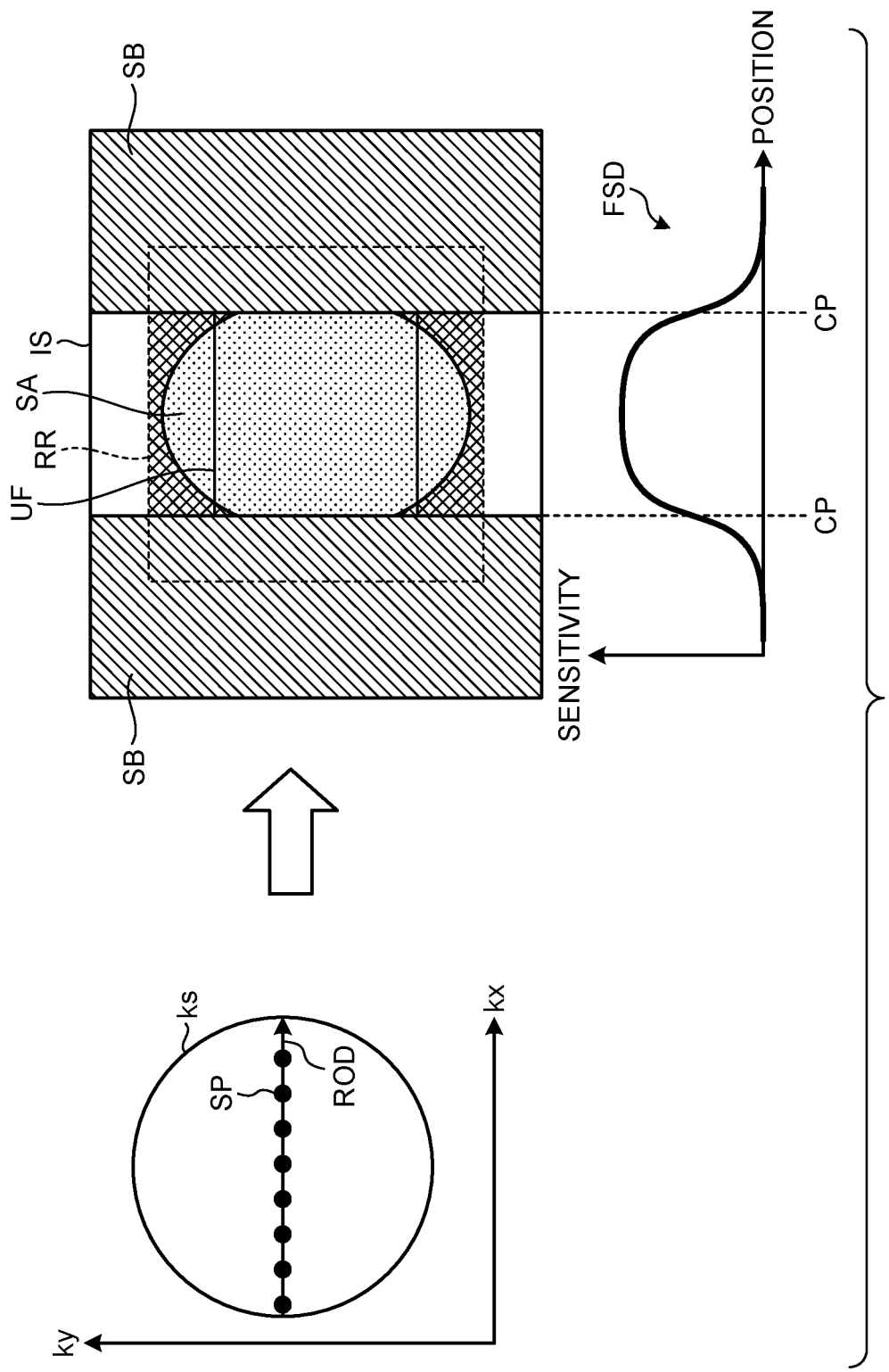

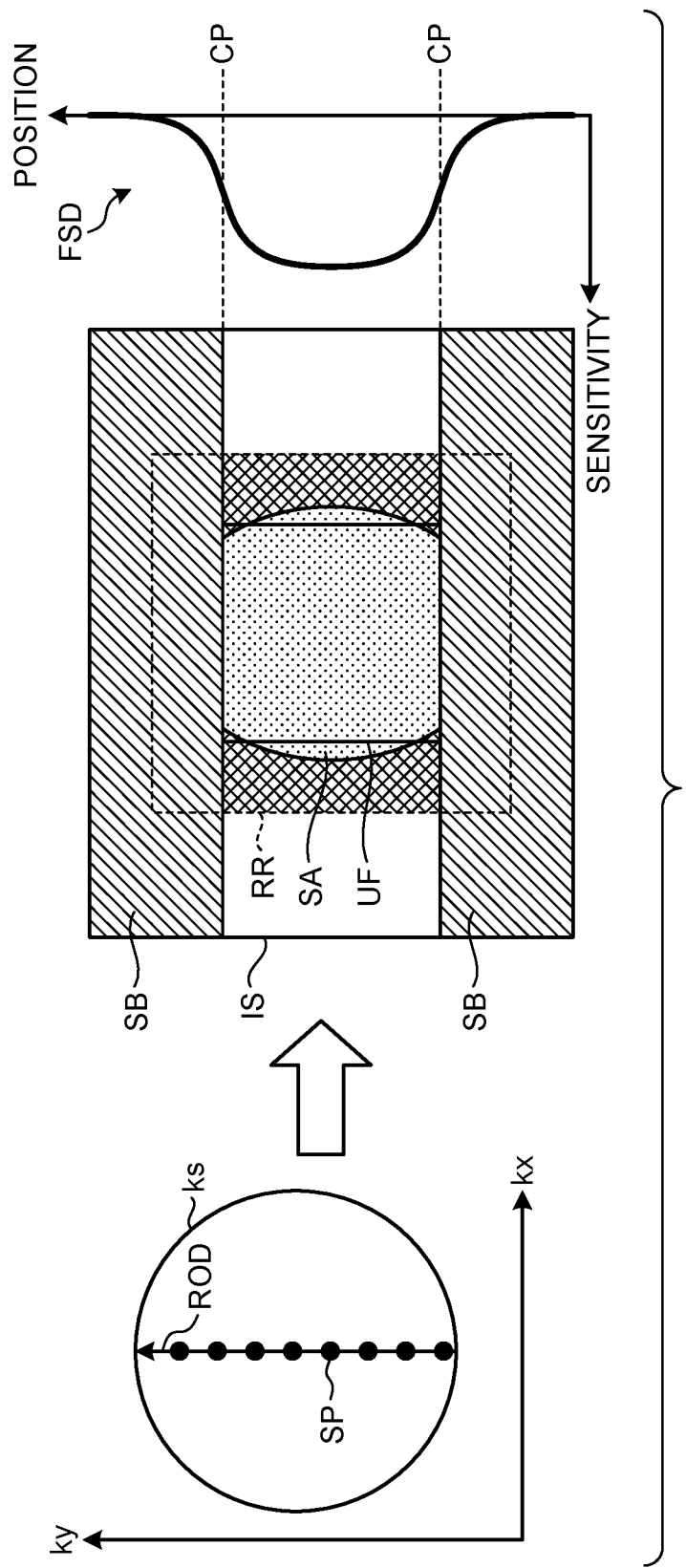

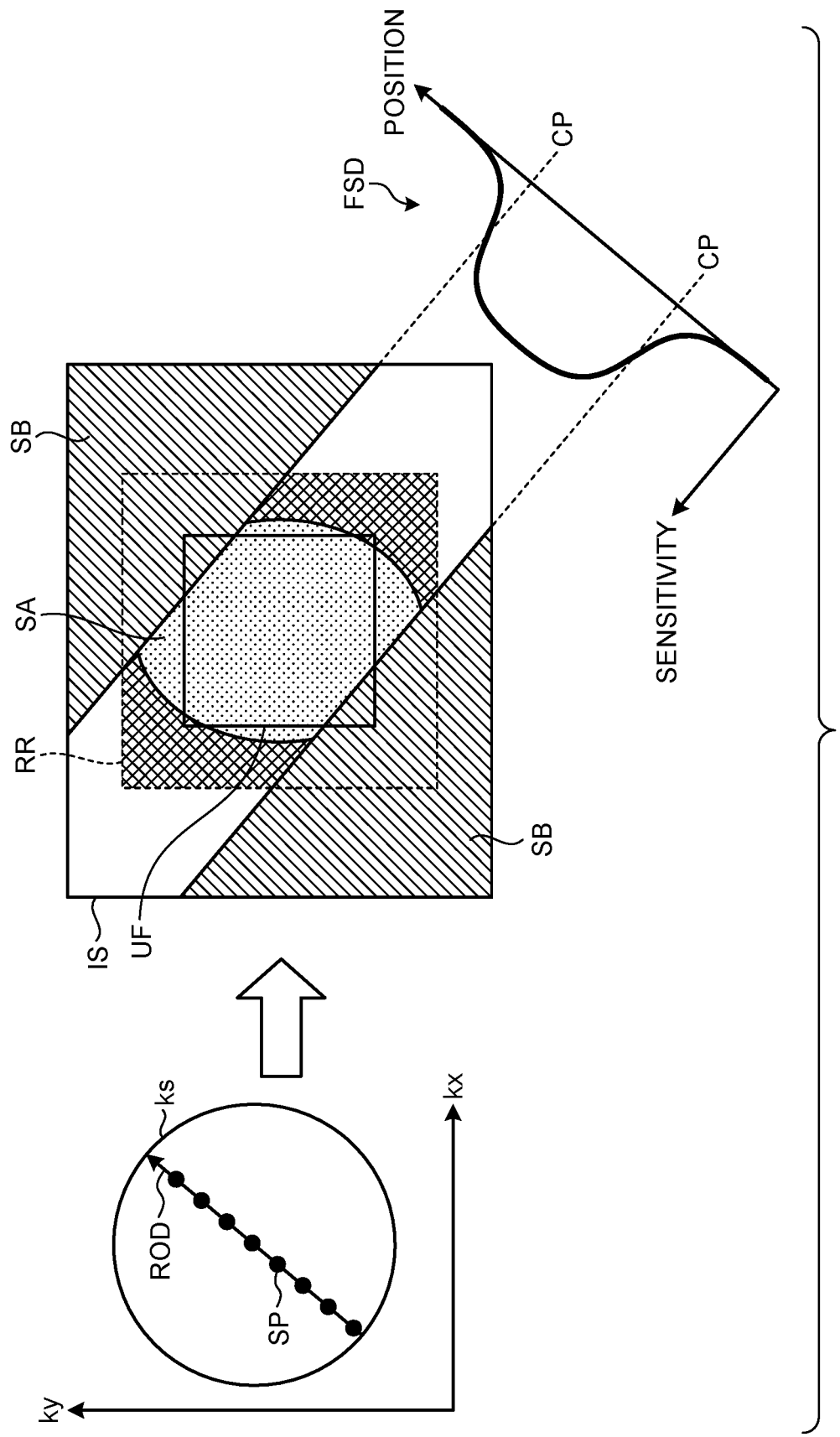

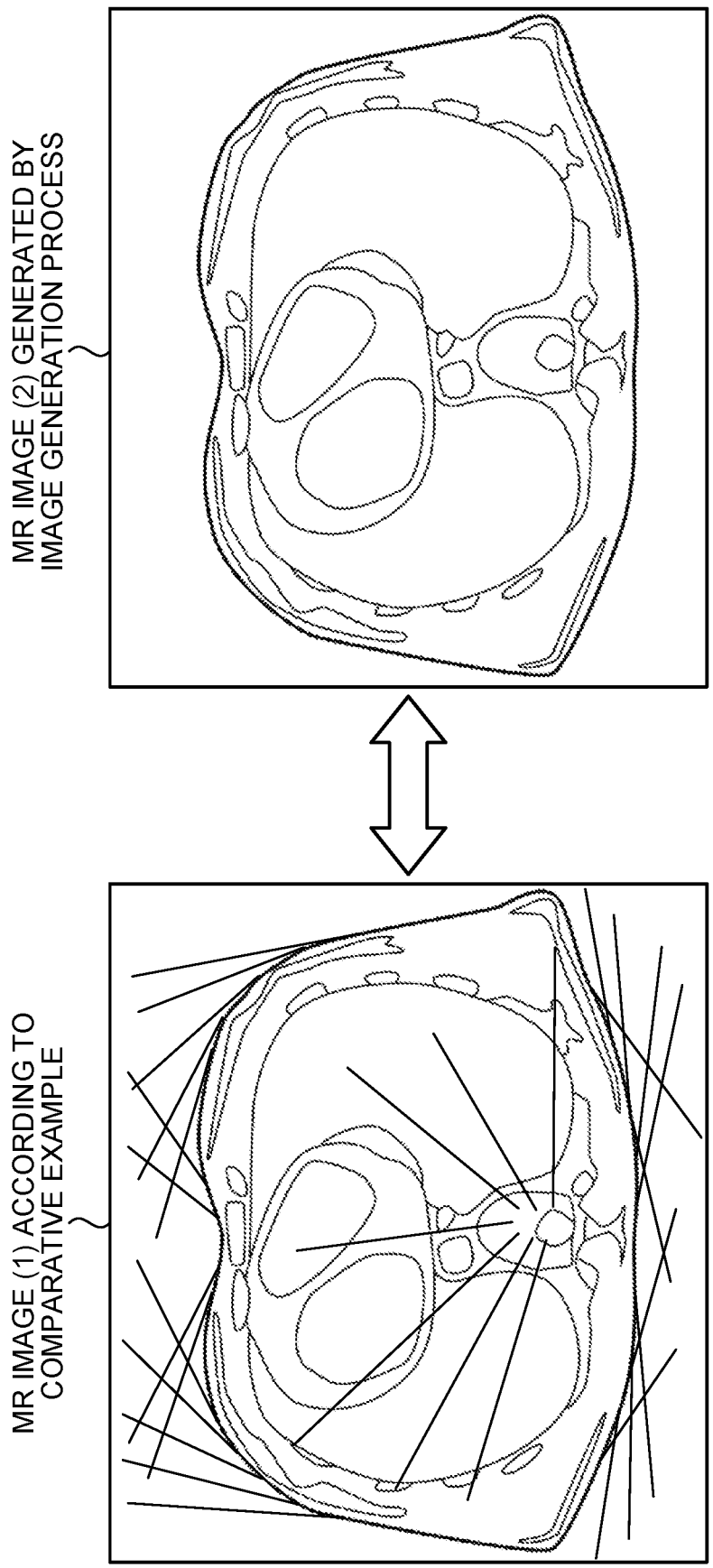

IMAGE GENERATING APPARATUS, IMAGE GENERATION METHOD, AND NONTRANSITORY COMPUTER-READABLE STORAGE MEDIUM STORING THEREIN IMAGE GENERATION PROGRAM

CROSS-REFERENCE TO RELATED APPLICATIONS

This application is based upon and claims the benefit of priority from Japanese Patent Application No. 2020-204769, filed on Dec. 10, 2020; the entire contents of which are incorporated herein by reference.

FIELD

Embodiments described herein relate generally to an image generating apparatus, an image generation method, and a non-transitory computer-readable storage medium storing therein an image generation program.

BACKGROUND

Magnetic resonance imaging (hereinafter, referred to as MRI) apparatuses have common problems in imaging, including aliasing in an image due to insufficiency of a sampling rate for received magnetic resonance (hereinafter, referred to as MR) signals (that is, insufficiency of a field of view corresponding to the reciprocal of a sampling interval). To address this problem, there have been developed some technologies, such as setting a low-pass filter with a sampling rate and oversampling the MR signals.

If the low-pass filter according to the technologies is used for the MR signals in scanning performed in varying read-out directions, such as radial scanning, the number of signals cut off by the low-pass filter varies depending on the read-out directions. This impairs the consistency of MR data disposed in a k-space between the different read-out directions. As a result, noise, such as streaky artifacts called streaks, occurs in an MR image generated by scanning performed in varying read-out directions, thereby deteriorating image quality. To prevent deterioration of image quality, it is necessary to expand a transmission (pass) band of the low-pass filter (low-frequency pass filter). The passband of the low-pass filter, however, cannot be sufficiently expanded (should not be expanded) because of performance limitations of MRI apparatuses and trade-off for reduction in the signal-noise ratio (S/N), for example.

BRIEF DESCRIPTION OF THE DRAWINGS

FIG. 6 is a diagram of an example of MR data in a k-space, a signal area, a user FOV, a reconstruction region, stopbands, and cut-off positions corresponding to cutoff frequencies in an image space, and a filter sensitivity distribution according to the embodiment;

FIG. 7 is a diagram of an example of the MR data in the k-space, the signal area, the user FOV, the reconstruction region, the stopbands, and the cut-off positions corresponding to the cutoff frequencies in the image space, and the filter sensitivity distribution according to the embodiment;

FIG. 8 is a diagram of an example of the MR data in the k-space, the signal area, the user FOV, the reconstruction region, the stopbands, and the cut-off positions corresponding to the cutoff frequencies in the image space, and the filter sensitivity distribution according to the embodiment; and FIG. 9 is a diagram of an example of an MR image generated by performing an existing reconstruction method on MR data according to a comparative example and an MR image generated by image generation process according to the present embodiment.

DETAILED DESCRIPTION

Figure 1:
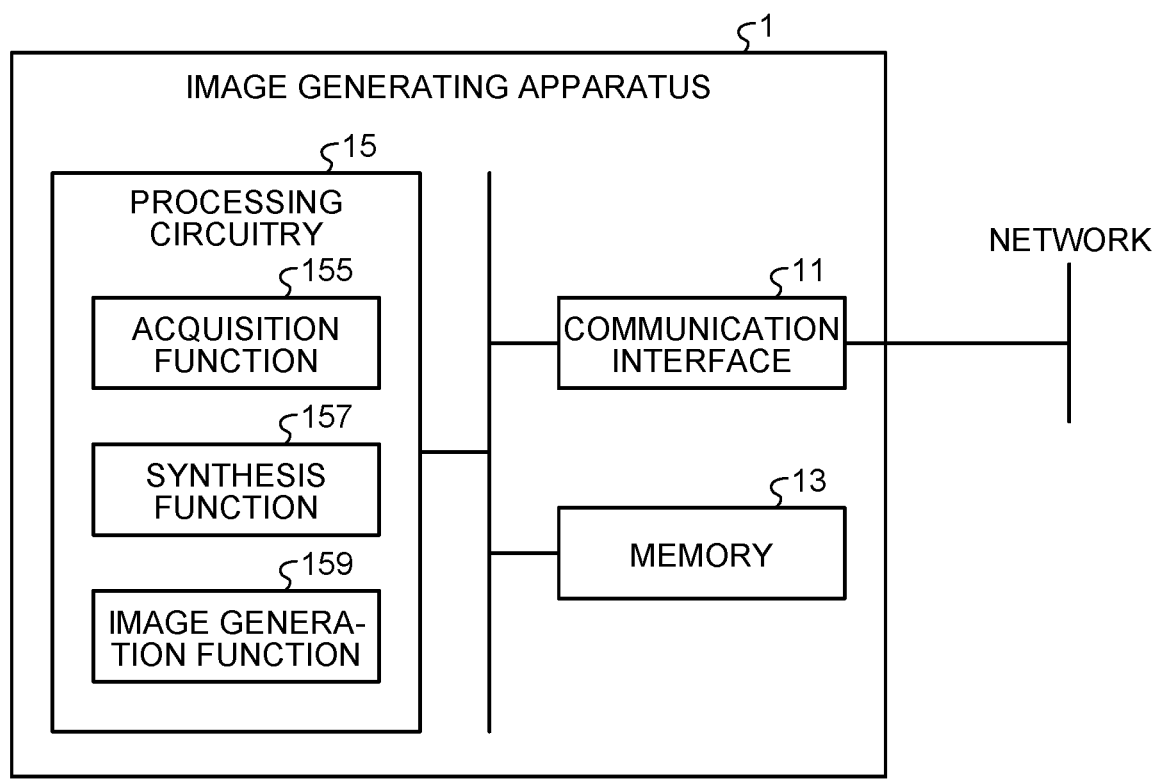
FIG. 1 is a block diagram of an example of an image generating apparatus according to an embodiment.

Exemplary embodiments of an image generating apparatus, an image generation method, and an image generation program are described below in greater detail with reference to the accompanying drawings. FIG. 1 is a block diagram of an example of an image generating apparatus 1. The image generating apparatus 1 is mounted on modalities or servers in hospital having various functions of the image generating apparatus 1, for example. The various functions of the image generating apparatus 1 may be mounted on servers of picture archiving and communication systems (hereinafter, referred to as PACS) or servers of a hospital information system (hereinafter, referred to as HIS), for example.

Modalities are medical diagnostic imaging apparatuses relating to magnetic resonance imaging (hereinafter, referred to as MRI), such as MRI apparatuses, positron emission tomography (PET)-MRI apparatuses, and single photon emission computed tomography (SPECT)-MRI apparatuses. To make the following description specific, the image generating apparatus 1 is assumed to be mounted on an MRI apparatus. The MRI apparatus has various functions of processing circuitry 15.

An image generating apparatus according to the embodiment includes processing circuitry. The processing circuitry acquires magnetic resonance data acquired in a plurality of read-out directions including a first read-out direction and a second read-out direction intersecting the first read-out direction, a plurality of filter sensitivity distributions corresponding to the read-out directions and indicating distributions of sensitivity of a low-pass filter, and a plurality of coil sensitivity distributions corresponding to a plurality of coil elements used to acquire the magnetic resonance data. The processing circuitry generates synthesis sensitivity distributions for the respective read-out directions by synthesizing the filter sensitivity distributions and the coil sensitivity distributions for the respective read-out directions. The processing circuitry generates a magnetic resonance image based on the synthesis sensitivity distributions and the magnetic resonance data.

EMBODIMENTS

Figure 2:
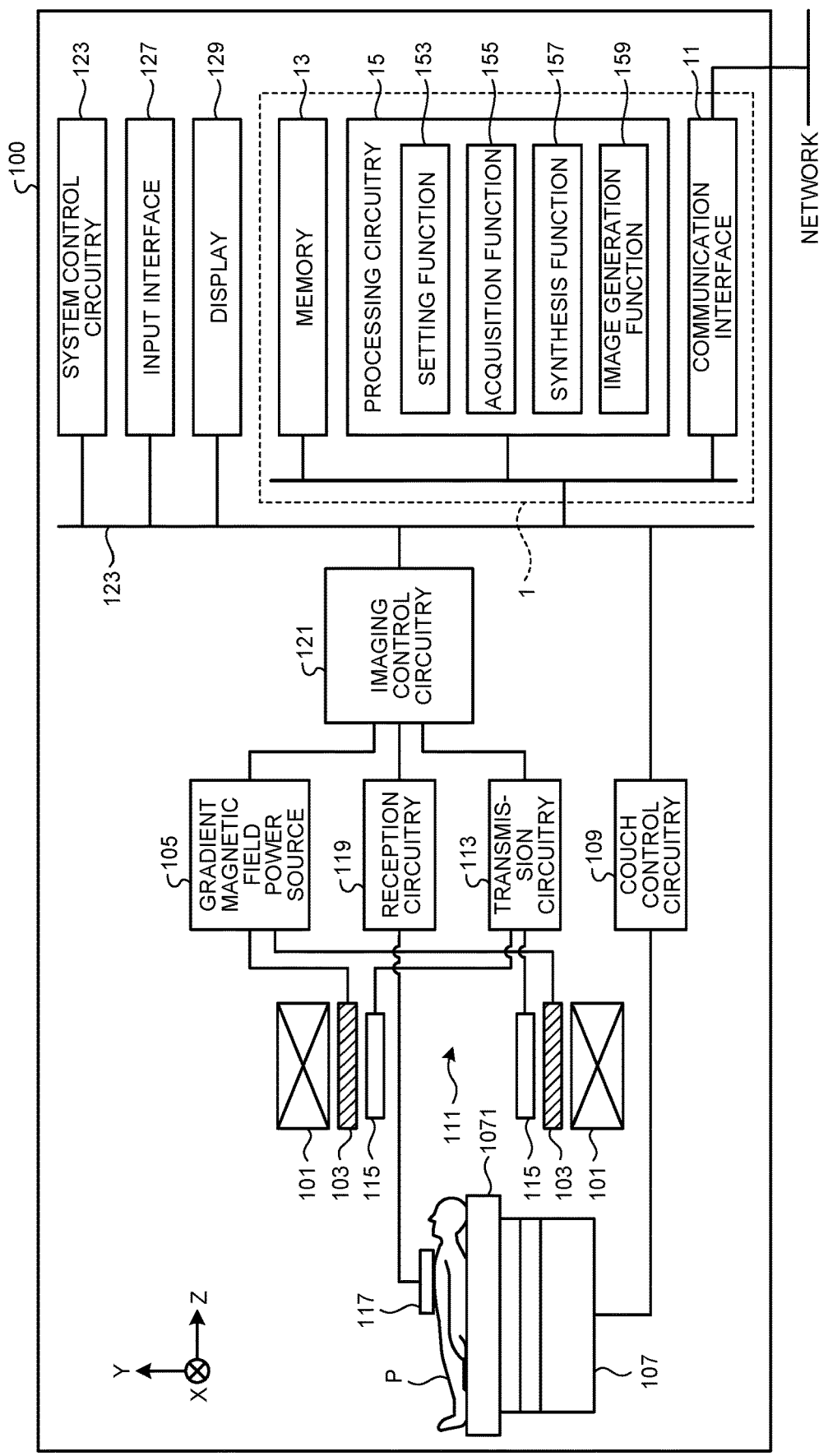
FIG. 2 is a block diagram of an example of a magnetic resonance imaging apparatus according to the embodiment.

FIG. 2 is a diagram of an example of an MRI apparatus 100 according to the present embodiment. As illustrated in FIG. 2, the MRI apparatus 100 includes a static magnetic field magnet 101, a gradient coil 103, a gradient magnetic field power source 105, a couch 107, couch control circuitry 109, transmission circuitry 113, a transmission coil 115, a reception coil 117, reception circuitry 119, imaging control circuitry (imaging controller) 121, system control circuitry (system controller) 123, a memory 13, an input interface 127, a display 129, a communication interface 11, and the processing circuitry 15. The image generating apparatus 1 may include the input interface 127 and the display 129 besides the communication interface 11, the memory 13, and the processing circuitry 15.

The static magnetic field magnet 101 is a hollow magnet having a substantially tubular shape. The static magnetic field magnet 101 generates a substantially uniform static magnetic field in the internal space. The static magnetic field magnet 101 is a superconducting magnet, for example.

The gradient coil 103 is a hollow coil having a substantially tubular shape and is disposed on the inner surface of a tubular cooling container. The gradient coil 103 independently receives an electric current from the gradient magnetic field power source 105 and generates a gradient magnetic field having magnetic field intensity that changes along X-, Y-, and Z-axes orthogonal to one another. The gradient magnetic field in the X-, Y-, and Z-axes generated by the gradient coil 103 forms a slice selection gradient magnetic field, a phase encoding gradient magnetic field, and a frequency encoding gradient magnetic field, for example. The slice selection gradient magnetic field is used to optionally determine an imaging section. The phase encoding gradient magnetic field is used to change the phase of magnetic resonance signals (hereinafter, referred to as MR signals) depending on the spatial position. The frequency encoding gradient magnetic field is used to change the frequency of MR signals depending on the spatial position.

The gradient magnetic field power source 105 is a power supply apparatus that supplies an electric current to the gradient coil 103 under the control of the imaging control circuitry 121.

The couch 107 is a apparatus including a couchtop 1071 on which a subject P is placed. The couch 107 inserts the couchtop 1071 with the subject P placed thereon into a bore 111 under the control of the couch control circuitry 109.

The couch control circuitry 109 controls the couch 107. The couch control circuitry 109 drives the couch 107 based on an instruction given by an operator through an input/output interface 17, thereby moving the couchtop 1071 in the longitudinal and vertical directions and the horizontal direction in some cases.

The transmission circuitry 113 supplies high frequency pulses modulated at the Larmor frequency to the transmission coil 115 under the control of the imaging control circuitry 121. The transmission circuitry 113 includes an oscillating unit, a phase selecting unit, a frequency converting unit, an amplitude modulating unit, and an RF amplifier, for example. The oscillating unit generates RF pulses at a resonance frequency unique to a target atomic nucleus in the static magnetic field. The phase selecting unit selects the phase of the RF pulses generated by the oscillating unit. The frequency converting unit converts the frequency of the RF pulses output from the phase selecting unit. The amplitude modulating unit modulates the amplitude of the RF pulses output from the frequency converting unit based on the sinc function, for example. The RF amplifier amplifies the RF pulses output from the amplitude modulating unit and supplies them to the transmission coil 115.

The transmission coil 115 is a radio frequency (RF) coil disposed on the inner side of the gradient coil 103. The transmission coil 115 generates RF pulses corresponding to a high frequency magnetic field due to output from the transmission circuitry 113.

The reception coil 117 is an RF coil disposed on the inner side of the gradient coil 103. The reception coil 117 receives MR signals output from the subject P by the high frequency magnetic field. The reception coil 117 outputs the received MR signals to the reception circuitry 119. The reception coil 117 is a coil array including one or more coil elements, typically, a plurality of coil elements, for example. To make a specific explanation, the following describes the reception coil 117 as a coil array including a plurality of coil elements.

The reception coil 117 may be composed of one coil element. While the transmission coil 115 and the reception coil 117 are illustrated as different RF coils in FIG. 2, they may be provided as an integrated transmission/reception coil. The transmission/reception coil is a local transmission/reception RF coil, such as a head coil, corresponding to an imaging region of the subject P.

The reception circuitry 119 generates digital MR signals (hereinafter, referred to as MR data) based on the MR signals output from the reception coil 117 under the control of the imaging control circuitry 121. Specifically, the reception circuitry 119 performs signal processing, such as wave detection and filtering, on the MR signals output from the reception coil 117. Subsequently, the reception circuitry 119 performs analog to digital (A/D) conversion (hereinafter, referred to as A/D conversion) on the data resulting from the signal processing to generate MR data. The reception circuitry 119 outputs the generated MR data to the imaging control circuitry 121. The MR data, for example, is generated for each coil element and is output to the imaging control circuitry 121 with a tag for identifying the coil element.

Figure 3:
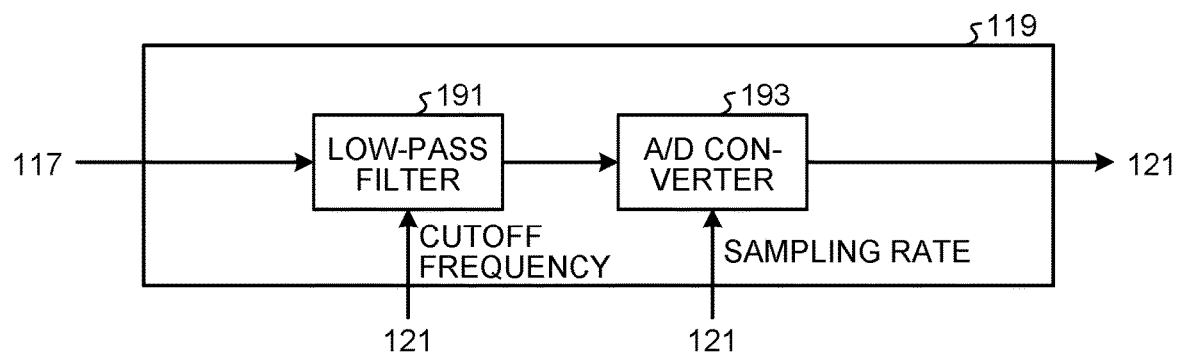
FIG. 3 is a diagram of an exemplary configuration of reception circuitry according to the embodiment.

FIG. 3 is a diagram of an example of the reception circuitry 119. The reception circuitry 119 includes a low-pass filter (low-frequency pass filter) 191 and an A/D converter 193. The reception circuitry 119 may also include various kinds of circuitry, such as a wave detector that performs the signal processing, besides the low-pass filter 191 and the A/D converter 193.

The low-pass filter 191 receives a cutoff (cut-off) frequency set by a setting function 153 via the imaging control circuitry 121. In other words, the passband of the low-pass filter 191 is set by the setting function 153. The cutoff frequency may be directly transmitted from the processing circuitry 15 to the low-pass filter 191. The low-pass filter 191 uses the received cutoff frequency to filter the MR signals.

The A/D converter 193 receives a sampling rate set by the setting function 153 via the imaging control circuitry 121. In other words, the sampling interval of The A/D converter 193 is set by the setting function 153. The A/D converter 193 samples the MR signals having passed through the low-pass filter 191 at a sampling timing corresponding to the sampling rate. As a result, the A/D converter 193 generates MR data.

The imaging control circuitry 121 controls the gradient magnetic field power source 105, the transmission circuitry 113, the reception circuitry 119, and other components according to an imaging protocol output from the processing circuitry 15 and performs imaging on the subject P. The imaging protocol has a pulse sequence corresponding to the type of an examination. The imaging protocol defines the magnitude of an electric current supplied to the gradient coil 103 by the gradient magnetic field power source 105, the timing at which the gradient magnetic field power source 105 supplies the electric current to the gradient coil 103, the magnitude and the time width of high frequency pulses supplied to the transmission coil 115 by the transmission circuitry 113, the timing at which the transmission coil 115 supplies the high frequency pulses to the transmission coil 115, and the timing at which the reception coil 117 receives MR signals, for example. When the imaging control circuitry 121 images the subject P by driving the gradient magnetic field power source 105, the transmission circuitry 113, the reception circuitry 119, and other components and receives MR data from the reception circuitry 119, it stored the received MR data in the memory 13.

The imaging control circuitry 121 executes the pulse sequence for imaging, thereby acquiring MR data. Imaging performed by the present embodiment corresponds to scanning for acquiring a plurality of MR signals corresponding to a plurality of read-out directions including a first read-out direction and a second read-out direction intersecting the first read-out direction.

Figure 4:
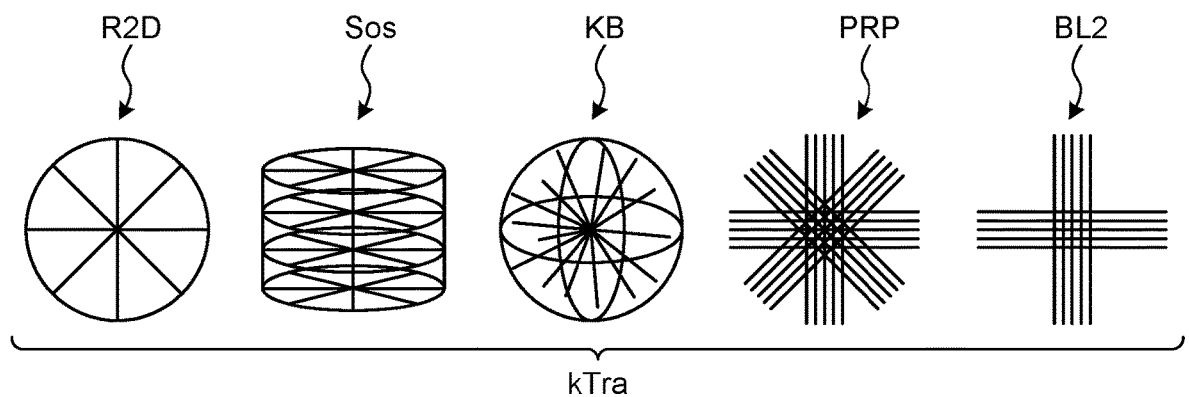
FIG. 4 is a diagram of an example of trajectories in a k-space relating to read-out of MR signals in main scanning according to the embodiment.

FIG. 4 is a diagram of an example of trajectories kTra in a k-space relating to read-out of MR signals in main scanning. Examples of the main scanning include, but are not limited to, two-dimensional radial acquisition R2D, three-dimensional radial acquisition (stack-of-stars) Sos, kooshball (KB), periodically rotated overlapping parallel lines with enhanced reconstruction (PROPELLER) acquisition PRP, acquisition BL2 with two blades, etc., as illustrated in FIG. 3.

To make a specific explanation, the following describes the main scanning as two-dimensional radial acquisition R2D. The two-dimensional radial acquisition R2D is hereinafter simply referred to as radial acquisition. The number of times of read-out in radial acquisition performed on the subject P as the main scanning, that is, the number of trajectories kTra in the read-out directions are set in advance before the main scanning.

The imaging control circuitry 121 acquires MR data (hereinafter, referred to as sensitivity data) relating to generation of a plurality of coil sensitivity distributions by a desired imaging method. The coil sensitivity distributions correspond to a plurality of coil elements used to acquire the MR data and indicate the distributions of sensitivity of the coil elements. The coil sensitivity distributions are expressed by complex numbers of data. The sensitivity data is acquired by the imaging control circuitry 121 in pre-scanning including locator scanning performed before the radial acquisition R2D performed as the main scanning, for example. The imaging control circuitry 121 is provided as a processor, for example.

The term "processor" means circuitry, such as a CPU, a graphics processing unit (GPU), an application specific integrated circuit (ASIC), a programmable logic device (e.g., a simple programmable logic device (SPLD)), a complex programmable logic device (CPLD), and a field programmable gate array (FPGA).

The system control circuitry 123 includes a processor and memories, such as a read-only memory (ROM) and a random access memory (RAM), which are not illustrated as hardware resources, and controls the MRI apparatus 100 by a system control function. Specifically, the system control circuitry 123 reads out a system control program stored in the memory and loads it on the memory. The system control circuitry 123 controls the circuitry of the MRI apparatus 100 according to the loaded system control program.

The system control circuitry 123, for example, reads out the imaging protocol from the memory 13 based on imaging conditions input by the operator through the input interface 127. The system control circuitry 123 transmits the imaging protocol to the imaging control circuitry 121 and controls imaging on the subject P. The system control circuitry 123 is provided as a processor, for example. The system control circuitry 123 may be incorporated in the processing circuitry 15. In this case, the processing circuitry 15 carries out the system control function and functions as an alternative to the system control circuitry 123. The processor serving as the system control circuitry 123 is not explained herein because it has the same configuration as that described above.

The memory 13 stores therein various computer programs relating to the system control function carried out by the system control circuitry 123, various imaging protocols, and imaging conditions including a plurality of imaging parameters defining the imaging protocols, for example. The memory 13 also stores therein the setting function 153, an acquisition function 155, a synthesis function 157, and an image generation function 159 implemented by the processing circuitry 15 as computer-executable programs.

The memory 13 stores therein MR images generated by the image generation function 159 and pre-scanning images generated by pre-scanning, such as locator scanning. The pre-scanning images include a positioning image (also referred to as a locator image) for setting a field of view (hereinafter, referred to as an FOV) in the main scanning and a coil sensitivity distribution used to generate (reconstruct) an MR image in the main scanning, for example. In other words, the memory 13 stores therein a plurality of coil sensitivity distributions corresponding to the respective coil elements in the reception coil 117. The memory 13 also stores therein an FOV set in a locator image.

The memory 13 stores therein a sampling rate (also referred to as a sampling frequency) or a sampling interval used by the A/D converter 193 in the main scanning performed after the pre-scanning. The memory 13 also stores therein a cutoff frequency used by the low-pass filter 191 in the main scanning. The memory 13 also stores therein MR data relating to the main scanning and an algorithm for reconstructing an MR image based on the MR data.

The memory 13 may store therein various kinds of data received via a communication interface 11. The memory 13, for example, stores therein information (e.g., an imaging target region and a purpose of an examination) on an examination order for the subject P received from an information processing system, such as a radiology information system (RIS), in a medical institution.

The memory 13 is provided as a semiconductor memory element, such as a ROM, a RAM, and a flash memory, a hard disk drive (HDD), a solid state drive (SSD), or an optical disc, for example. The memory 13 may be provided as a drive device or the like that reads and writes various kinds of information from and to a portable storage medium, such as a compact disc (CD)-ROM drive, a digital versatile disc (DVD) drive, and a flash memory.

The input interface 127 receives various instructions (e.g., a power-on instruction) and information from the operator. The input interface 127 is provided as a trackball, a switch button, a mouse, a keyboard, a touch pad on which the operator performs an input operation by touching an operating screen, a touch screen that integrates a display screen and a touch pad, contactless input circuitry provided with an optical sensor, or voice input circuitry, for example. The input interface 127 is coupled to the processing circuitry 15. The input interface 127 converts an input operation received from the operator into electrical signals and outputs them to the processing circuitry 15. The input interface 127 in the present specification is not limited to a component including physical operating parts, such as a mouse and a keyboard. The input interface 127 may be processing circuitry that receives electrical signals corresponding to an input operation from an external input device provided separately from the MRI apparatus 100 and outputs the electrical signals to the control circuitry, for example.

The input interface 127 inputs an FOV to a locator image displayed on the display 129 based on an instruction given by a user. Specifically, the input interface 127 inputs an FOV based on an instruction for setting a range by the user in a locator image displayed on the display 129. The input interface 127 inputs various imaging parameters relating to the main scanning according to an instruction giving by the user based on the examination order.

The display 129 displays various graphical user interfaces (GUI), an MR image generated by the processing circuitry 15, a pre-scanning image, such as a locator image, and other images under the control of the processing circuitry 15 or the system control circuitry 123. The display 129 also displays an imaging parameter image relating to the main scanning and the pre-scanning and various kinds of information relating to image processing, for example. The display 129 is provided as a display device, such as a CRT display, a liquid crystal display, an organic EL display, an LED display, a plasma display, or other desired displays or monitors known in the present technical field.

The communication interface 11 performs data communications with HIS and PACS, for example. Any desired communication standard may be employed for the communications between the communication interface 11 and the hospital information system. Examples of the communication standard include, but are not limited to, Health Level Seven (HL7), DICOM, both of them, etc. The communication interface 11 receives information (e.g., an imaging target region and a purpose of an examination) on an examination order for the subject P received from an information processing system, such as RIS, in a medical institution. If the image generating apparatus 1 is not mounted on the MRI apparatus 100, the communication interface 11 in the image generating apparatus 1 receives MR data from the MRI apparatus 100 or the like that images the subject P in an examination on the subject P. The received MR data is stored in the memory 13.

The processing circuitry 15 is provided as the processor described above, for example. The processing circuitry 15 includes the setting function 153, the acquisition function 155, the synthesis function 157, and the image generation function 159, for example. The processing circuitry 15 that implements the setting function 153, the acquisition function 155, the synthesis function 157, and the image generation function 159 corresponds to a setting unit, an acquiring unit, a synthesizing unit, and an image generating unit. Various functions, such as the setting function 153, the acquisition function 155, the synthesis function 157, and the image generation function 159, are stored in the memory 13 as computer-executable programs. The processing circuitry 15, for example, reads out a computer program from the memory 13 and executes it, thereby implementing the function corresponding to the computer program. In other words, the processing circuitry 15 that has read out the computer programs has various functions, such as the setting function 153, the acquisition function 155, the synthesis function 157, and the image generation function 159.

While the "processor" reads out the computer programs corresponding to the respective functions from the memory 13 and executes them in the description above, the embodiment is not limited thereto. If the processor is a CPU, for example, the processor reads out a computer program stored in the memory 13 and executes it, thereby implementing the corresponding function. If the processor is an ASIC, the computer program is not stored in the memory 13, and the function is directly incorporated in the circuitry of the processor as a logic circuit. The processors according to the present embodiment do not necessarily each provided as single circuitry. Alternatively, a plurality of independent circuitry may be combined to serve as one processor and implement the functions. While the single storage circuitry stores therein the computer programs corresponding to the respective processing functions in the description above, the embodiment is not limited thereto. A plurality of storage circuitry may be dispersed and disposed, and the processing circuitry 15 may read out a computer program from the corresponding storage circuitry.

The setting function 153 of the processing circuitry 15 sets a sampling rate based on an FOV (hereinafter, referred to as a user FOV) input by the user. Specifically, the setting function 153 sets the sampling rate using the reciprocal of the user FOV as a sampling interval. The setting function 153 outputs the set sampling rate to the A/D converter 193 via the imaging control circuitry 121. As a result, the MR data is generated by sampling the MR signals at the sampling rate set based on the field of view.

The setting function 153 may multiply the reciprocal of the size of the user FOV by a constant, thereby setting a sampling rate corresponding to oversampling (hereinafter, referred to as an oversampling rate). The upper limit of the oversampling rate (hereinafter, referred to as an upper limit rate) is set in advance based on performance limitations of the MRI apparatus 100. The setting function 153 sets the oversampling rate below the upper limit rate. The MR data generated by the reception circuitry 119 corresponds to k-space data obtained by sampling the MR signals at the sampling rate determined based on the user FOV or the oversampling rate (sampling rate higher than the sampling rate corresponding to the field of view input by the user).

Oversampling corresponds to expanding the field of view compared with the user FOV. Oversampling is performed when it is necessary to increase the acquisition rate, including the case where the user FOV set in the pre-scanning image is smaller than an area in which protons, such as water molecules, are present in an imaging space. A reconstruction region is determined based on the expanded FOV. To make the following description specific, the sampling rate is assumed to be the reciprocal of the user FOV.

The setting function 153 of the processing circuitry 15 sets a cutoff frequency defining a passband for MR signals in the low-pass filter 191 based on the set sampling rate. Specifically, the setting function 153 sets the cutoff frequency based on the user FOV in the main scanning performed on the subject P in a plurality of read-out directions and the intensity of the gradient magnetic field in the main scanning. The setting function 153, for example, sets a tentative cut-off frequency using the band of the low-pass filter 191 in the following expression:

User FOV[cm]=(2×Band[Hz]of Low-Pass Filter)/ Intensity of Read-Out Gradient Magnetic Field [Hz/cm]

In the expression, the intensity of the read-out gradient magnetic field corresponds to the intensity of the gradient magnetic field in the main scanning.

The setting function 153 generates filter sensitivity distributions indicating distributions of sensitivity of the low-pass filter 191 in the k-space for the respective read-out directions based on the set cutoff frequency and the read-out directions. The setting function 153 stores the filter sensitivity distributions corresponding to the respective read-out directions in the memory 13 in a manner associated with the respective read-out directions.

The acquisition function 155 of the processing circuitry 15 acquires MR data acquired in a plurality of read-out directions, a plurality of filter sensitivity distributions corresponding to the read-out directions, and a plurality of coil sensitivity distributions corresponding to a plurality of coil elements from the memory 13. The acquired MR data is acquired in the read-out directions including a first read-out direction and a second read-out direction intersecting the first read-out direction. The coil sensitivity distributions correspond to the coil elements in the reception coil 117 for acquiring MR data and indicate the distributions of sensitivity of the coil elements. The filter sensitivity distributions correspond to the read-out directions and indicate the distributions of sensitivity of the low-pass filter 191.

The synthesis function 157 of the processing circuitry 15 synthesizes the filter sensitivity distributions and the coil sensitivity distributions for the respective read-out directions. As a result, the synthesis function 157 generates synthesis sensitivity distributions for the respective read-out directions. The synthesis sensitivity distribution indicates the distribution of synthesis sensitivity obtained by synthesizing the sensitivity of the coil element and the sensitivity of the low-pass filter 191 for each of the read out directions. In other words, the synthesis function 157 generates a plurality of synthesis sensitivity distributions corresponding to the read-out directions. The specific contents of processing performed by the synthesis function 157 will be described later in greater detail in the description of processing of generating an MR image based on MR data acquired in the read-out directions including the first read-out direction and the second read-out direction intersecting the first read-out direction (hereinafter, referred to as image generation process).

The image generation function 159 of the processing circuitry 15 acquires MR data (hereinafter, referred to as pre-scanning data) generated by pre-scanning performed on the subject P from the reception circuitry 119 and disposes it in a k-space. The image generation function 159 generates a pre-scanning image based on the pre-scanning data disposed in the k-space. The image generation function 159 stores the generated pre-scanning image in the memory 13.

The image generation function 159 of the processing circuitry 15, for example, acquires MR data generated by scanning for generating a locator image from the reception circuitry 119 and disposes it in a k-space. The image generation function 159 generates (reconstructs) a locator image based on the MR data disposed in the k-space. The image generation function 159 acquires sensitivity data generated by scanning for generating a sensitivity map from the reception circuitry 119 and disposes it in a k-space. The image generation function 159 generates (reconstructs) a sensitivity map based on the sensitivity data disposed in the k-space. Generating the locator image, the sensitivity map, and other data is not explained herein because it can be performed using an existing reconstruction method.

The image generation function 159 of the processing circuitry 15 generates an MR image corresponding to the main scanning based on the synthesis sensitivity distributions and the MR data. The image generation function 159, for example, generates the MR image by performing sensitivity encoding (hereinafter, referred to as SENSE) using the synthesis sensitivity distributions on the MR data. The image generation function 159 may generate the MR image using a regularization term relating to compressed sensing (CS) or super resolution as a regularization term relating to generation of the MR image. The specific contents of processing performed by the image generation function 159 will be described later in the image generation process.

Figure 5:
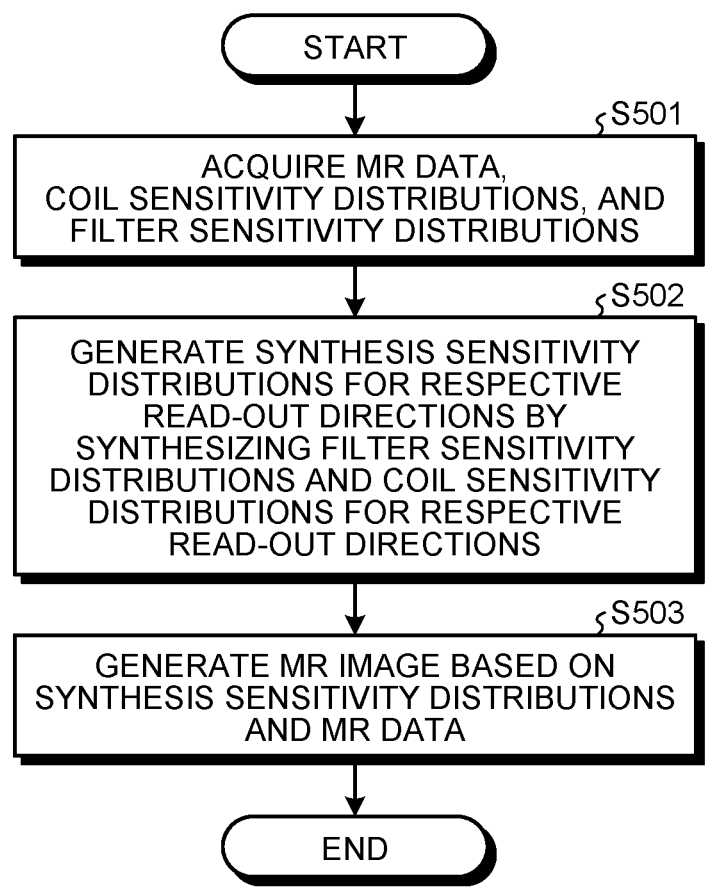
FIG. 5 is a flowchart of an example of a process of image generation process according to the embodiment.

The following describes image generation process performed by the MRI apparatus 100 and the image generating apparatus 1 according to the present embodiment having the configuration described above with reference to FIGS. 5 to 8. FIG. 5 is a flowchart of an example of a process of image generation process. The following describes various kinds of processing performed before image generation process first and then describes the image generation process.

The imaging control circuitry 121 performs pre-scanning on the subject P. An image generation function 161 of the processing circuitry 15 generates a pre-scanning image based on pre-scanning data. The image generation function 161 stores the generated pre-scanning image, such as a locator image and a coil sensitivity image, in the memory 13. The system control circuitry 123 displays the locator image on the display 129.

The input interface 127 inputs an FOV (hereinafter, referred to as the user FOV) in the locator image based on an instruction given by the user. The user FOV is stored in the memory 13. The setting function 153 of the processing circuitry 15 sets a sampling rate based on the user FOV and outputs the set sampling rate to the A/D converter 193 before the main scanning.

The setting function 153 of the processing circuitry 15 sets a cutoff frequency of the low-pass filter 191 to be applied to MR signals received in the main scanning. Specifically, the setting function 153 sets a cutoff frequency based on the intensity of the gradient magnetic field in the main scanning and the user FOV. The setting function 153 outputs the set cutoff frequency to the low-pass filter 191.

The imaging control circuitry 121 performs radial acquisition as the main scanning on the subject P. Specifically, the imaging control circuitry 121 performs imaging along one read-out direction in the main scanning. As a result, the reception coil 117 receives MR signals in the read-out direction. The MR signals received by the reception coil 117 are output to the reception circuitry 119. At this time, the MR signals are detected by a wave detector.

The low-pass filter 191 filters the MR signals resulting from wave detection using the set cutoff frequency. Filtering the MR signals by the low-pass filter 191 reduces the number of unnecessary signals outside the user FOV. As a result, the S/N of the MR signals and the like is improved. The MR signals resulting from filtering are output to the A/D converter 193.

The A/D converter 193 samples the MR signals output from the low-pass filter 191 using the sampling rate set by the setting function 153. As a result, the A/D converter 193 generates MR data. In other words, the A/D converter 193 performs A/D conversion on the MR signals having passed through the low-pass filter 191 at the sampling rate, thereby generating MR data. The MR data is stored in the memory 13 via the imaging control circuitry 121. If acquisition of the MR signals is completed in all the read-out directions (corresponding to the total number of trajectories kTra in the read-out directions) set in advance in the main scanning, image generation process is started.

Image Generation Process

Step S501

The acquisition function 155 of the processing circuitry 15 acquires the MR data generated in the main scanning, the coil sensitivity distributions generated in the pre-scanning performed before the main scanning, and the filter sensitivity distributions corresponding to the read-out directions from the memory 13. If the image generating apparatus 1 is not mounted on the MRI apparatus 100, the acquisition function 155 acquires the MR data, the coil sensitivity distributions, and the filter sensitivity distributions from various MRI apparatuses via the communication interface 11 and a network.

FIG. 6 is a diagram of an example of a read-out direction ROD and sampling points SP in a k-space ks, a signal area SA, a user FOV UF, a reconstruction region RR, stopbands SB, and cut-off positions CP corresponding to cutoff frequencies in an image space IS, and a filter sensitivity distribution FSD. The signal area SA in FIG. 6 corresponds to an area in which protons, such as water molecules, are present in an imaging space. The stopbands SB each indicate a band in which the MR signals output from the reception coil 117 are stopped by the low-pass filter 191.

As illustrated in FIG. 6, the read-out direction ROD passes through the center of the k-space ks and is parallel to a kx direction. The user FOV UF illustrated in FIG. 6 corresponds to the sampling interval and is equal to the FOV defined by the sampling points SP disposed side by side. As illustrated in FIG. 6, the cut-off position CP corresponding to the cutoff frequency corresponds to an inflection point of a curve indicating the sensitivity in the filter sensitivity distribution FSD.

FIG. 7 is a diagram of an example of the read-out direction ROD and the sampling points SP in the k-space ks, the signal area SA, the user FOV UF, the reconstruction region RR, the stopbands SB, and the cut-off positions CP corresponding to the cutoff frequencies in the image space IS, and the filter sensitivity distribution FSD. FIG. 7 is different from FIG. 6 in that the read-out direction ROD in FIG. 7 passes through the center of the k-space ks and is parallel to a ky direction.

FIG. 8 is a diagram of an example of the read-out direction ROD and the sampling points SP in the k-space ks, the signal area SA, various kinds of FOV, the reconstruction region RR, the stopbands SB, and the cut-off positions CP corresponding to the cutoff frequencies in the image space IS, and the filter sensitivity distribution FSD. FIG. 8 is different from FIGS. 6 and 7 in that the read-out direction ROD in FIG. 8 passes through the center of the k-space ks and inclines at 45° with respect to the kx direction or the ky direction. As illustrated in FIGS. 6 to 8, the filter sensitivity distribution FSD has a semicircular distribution of sensitivity and varies depending on the read-out directions.

Step S502

The synthesis function 157 of the processing circuitry 15 generates synthesis sensitivity distributions for the respective read-out directions by synthesizing the filter sensitivity distributions and the coil sensitivity distributions for the respective read-out directions. When the coil sensitivity distribution in a coil element i is $S_i$, and the filter sensitivity distribution in a read-out direction $\vec{r}$ is $S_{\vec{r}}$, the synthesis function 157 calculates a synthesis sensitivity distribution $S_k$ in the k-th read-out direction in the main scanning as expressed by the following expression:

$$S_{\vec{r}} S_i$$

The synthesis sensitivity distribution $S_k$ in the expression above corresponds to masking the coil sensitivity distribution. The synthesis function 157 calculates the synthesis sensitivity distributions corresponding to the total number of coil elements for the respective read-out directions. The calculated synthesis sensitivity distributions $S_k$ are stored in the memory 13 in a manner associated with the respective read-out directions.

Step S503

The image generation function 159 of the processing circuitry 15 generates an MR image in the main scanning based on the synthesis sensitivity distribution $S_k$ and MR data. The image generation function 159, for example, generates the MR image by performing SENSE using the synthesis sensitivity distribution $S_k$ on the MR data as expressed by the following expression.

$$\mathrm{argmin}_x \left[ \sum_k \|F_k S_k x - y_k\|_2^2 + R(x) \right] \quad (1)$$

In the expression, x denotes data (main scanning image) in an image space in a field of view corresponding to the sampling rate of MR data or an expanded field of view, $F_k$ denotes Fourier transform in the k-th read-out direction, $y_k$ denotes MR data in the k-th read-out direction, $S_k$ denotes a synthesis sensitivity distribution in the k-th read-out direction, and R(x) denotes a regularization term relating to the main scanning image x. The L2 norm in Expression (1) takes into account cut-off of the MR signals by the low-pass filter 191, thereby securing consistency between the MR data and the MR image. In other words, the image generation function 159 can generate an image in a field of view larger than that corresponding to the sampling rate of the MR data by Expression (1).

If the coil sensitivity map is not used, the synthesis sensitivity distribution $S_k$ in the expression above is equal to the filter sensitivity distribution in the k-th read-out, and a formula corresponding to various assumptions relating to the main scanning image is incorporated in the regularization term R(x). The image generation function 159 determines x so as to satisfy Expression (1), thereby generating the main scanning image. The method for reconstructing the main scanning image by the image generation function 159 is not limited to SENSE. The image generation function 159 may generate the MR image using a regularization term relating to compressed sensing (CS) or super resolution as the regularization term R(x) relating to generation of the MR image in Expression (1), for example.

The image generation function 159 of the processing circuitry 15 stores the generated MR image in the memory 13. The system control circuitry 123 may display the generated MR image on the display 129. If the image generating apparatus 1 is not mounted on the MRI apparatus 100, the generated MR image is output to the servers of PACS and HIS, for example, via the communication interface 11 and the network.

As described above, the image generating apparatus 1 according to the embodiment described above acquires MR data acquired in a plurality of read-out directions including a first read-out direction and a second read-out direction intersecting the first read-out direction, a plurality of filter sensitivity distributions corresponding to the read-out directions and indicating distributions of sensitivity of the low-pass filter 191, and a plurality of coil sensitivity distributions corresponding to a plurality of coil elements used to acquire the MR data. The image generating apparatus 1 generates synthesis sensitivity distributions for the respective read-out directions by synthesizing the filter sensitivity distributions and the coil sensitivity distributions for the respective read-out directions. The image generating apparatus 1 generates an MR image based on the synthesis sensitivity distributions and the MR data. The size of the MR image generated by the image generating apparatus 1 can be larger than the field of view corresponding to the sampling rate of the MR data.

The image generating apparatus 1 according to the present embodiment, for example, generates the MR image by performing sensitivity encoding (SENSE) using the synthesis sensitivity distributions on the MR data. The image generating apparatus 1 according to the present embodiment may generate the MR image using a regularization term relating to compressed sensing (CS) as the regularization term R(x) relating to generation of the MR image.

As described above, the image generating apparatus 1 according to the present embodiment can generate the MR image while securing consistency between the MR data and the MR image by adding effects caused by the low-pass filter 191 in the k-space if the passband of the low-pass filter 191 cannot be sufficiently expanded because of performance limitations of the MRI apparatus 100 and trade-off for reduction in S/N. Consequently, the image generating apparatus 1 can acquire a high-quality image with fewer streaks.

FIG. 9 is a diagram of an example of an MR image (1) generated by performing an existing reconstruction method on MR data to which no effect of the low-pass filter 191 is added according to a comparative example and an MR image (2) generated by adding effects of the low-pass filter 191 by image generation process according to the present embodiment. As illustrated in FIG. 9, the MR image (2) generated by image generation process according to the present embodiment has fewer streak artifacts or the like and has higher image quality than the MR image (1). Consequently, the image generating apparatus 1 according to the present embodiment, as illustrated in FIG. 9, can generate an MR image having higher image quality in the main scanning if the passband of the low-pass filter 191 cannot be sufficiently expanded because of performance limitations of the MRI apparatus 100 and trade-off for reduction in S/N.

To implement the technical ideas according to the present embodiment by an image generation method, the image generation method includes: acquiring MR data acquired in a plurality of read-out directions including a first read-out direction and a second read-out direction intersecting the first read-out direction, a plurality of filter sensitivity distributions corresponding to the read-out directions and indicating distributions of sensitivity of the low-pass filter 191, and a plurality of coil sensitivity distributions corresponding to a plurality of coil elements used to acquire the MR data; generating synthesis sensitivity distributions for the respective read-out directions by synthesizing the filter sensitivity distributions and the coil sensitivity distributions for the respective read-out directions; and generating an MR image based on the synthesis sensitivity distributions and the MR data. The process and the advantageous effects of the image generation process according to the present image generation method are not explained herein because they are the same as those according to the embodiment.

To implement the technical ideas according to the present embodiment by an image generation program, the image generation program comprising instructions that cause a computer to execute: acquiring MR data acquired in a plurality of read-out directions including a first read-out direction and a second read-out direction intersecting the first read-out direction, a plurality of filter sensitivity distributions corresponding to the read-out directions and indicating distributions of sensitivity of the low-pass filter 191, and a plurality of coil sensitivity distributions corresponding to a plurality of coil elements used to acquire the MR data; generating synthesis sensitivity distributions for the respective read-out directions by synthesizing the filter sensitivity distributions and the coil sensitivity distributions for the respective read-out directions; and generating an MR image based on the synthesis sensitivity distributions and the MR data.

The image generation process can be performed by installing the image generation program on a computer in a modality, such as the MRI apparatus 100, and a PACS server and loading it on the memory, for example. The computer program that can cause the computer to perform the method may be stored and distributed in a storage medium, such as a magnetic disk (e.g., a hard disk), an optical disc (e.g., a CD-ROM and a DVD), and a semiconductor memory. The process and the advantageous effects of the image generation process performed by the image generation program are not explained herein because they are the same as those according to the embodiment.

At least one of the embodiments and the like described above can generate a magnetic resonance image having higher image quality. In other words, at least one of the embodiments and the like can generate an MR image on the k-space while securing consistency if the passband of the low-pass filter 191 cannot be sufficiently expanded in scanning performed in varying read-out directions. Consequently, at least one of the embodiments and the like can acquire a high-quality MR image with fewer streaks.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An image generating apparatus comprising:
    processing circuitry configured to
        acquire magnetic resonance data acquired in a plurality of read-out trajectory directions including a first read-out direction and a second read-out direction intersecting the first read-out direction, a plurality of filter sensitivity distributions corresponding to the read-out trajectory directions and indicating distributions of sensitivity of a low-pass filter, and a plurality of coil sensitivity distributions corresponding to a plurality of coil elements used to acquire the magnetic resonance data,
        generate synthesis sensitivity distributions for the respective read-out trajectory directions by synthesizing the filter sensitivity distributions and the coil sensitivity distributions for the respective read-out trajectory directions, and
        generate a magnetic resonance image based on the synthesis sensitivity distributions and the magnetic resonance data.

2. The image generating apparatus according to claim 1, wherein the size of the magnetic resonance image is larger than a field of view corresponding to a sampling rate of the magnetic resonance data.

3. The image generating apparatus according to claim 1, wherein the processing circuitry generates the magnetic resonance image by performing sensitivity encoding using the synthesis sensitivity distributions on the magnetic resonance data.

4. The image generating apparatus according to claim 1, wherein the processing circuitry generates the magnetic resonance image using a regularization term relating to compressed sensing.

5. The image generating apparatus according to claim 1, wherein the plurality of filter sensitivity distributions indicate the distributions of sensitivity of the low-pass filter in a k-space, and wherein a cutoff frequency of the low-pass filter is set based on a user field of view and an intensity of a gradient magnetic field.

6. An image generation method comprising:
acquiring magnetic resonance data acquired in a plurality of read-out trajectory directions including a first read-out direction and a second read-out direction intersecting the first read-out direction, a plurality of filter sensitivity distributions corresponding to the read-out trajectory directions and indicating distributions of sensitivity of a low-pass filter, and a plurality of coil sensitivity distributions corresponding to a plurality of coil elements used to acquire the magnetic resonance data;
generating synthesis sensitivity distributions for the respective read-out trajectory directions by synthesizing the filter sensitivity distributions and the coil sensitivity distributions for the respective read-out trajectory directions; and
generating a magnetic resonance image based on the synthesis sensitivity distributions and the magnetic resonance data.

7. A non-transitory computer-readable storage medium storing therein an image generation program comprising instructions that cause a computer to execute:
acquiring magnetic resonance data acquired in a plurality of read-out trajectory directions including a first read-out direction and a second read-out direction intersecting the first read-out direction, a plurality of filter sensitivity distributions corresponding to the read-out trajectory directions and indicating distributions of sensitivity of a low-pass filter, and a plurality of coil sensitivity distributions corresponding to a plurality of coil elements used to acquire the magnetic resonance data;
generating synthesis sensitivity distributions for the respective read-out trajectory directions by synthesizing the filter sensitivity distributions and the coil sensitivity distributions for the respective read-out trajectory directions; and
generating a magnetic resonance image based on the synthesis sensitivity distributions and the magnetic resonance data.

* * * * *